(12) United States Patent
Balmer et al.

(10) Patent No.: US 6,586,631 B1
(45) Date of Patent: Jul. 1, 2003

(54) ACETOACETARYLAMIDES

(75) Inventors: Bernard Balmer, Visp (CH); Sven Hafkesbrink, Termen (CH); Max Lauwiner, Brig (CH)

(73) Assignee: Lonza, Ltd., Gampel/Valais (CH)

( * ) Notice: Subject to any disclaimer, the term of this patent is extended or adjusted under 35 U.S.C. 154(b) by 256 days.

(21) Appl. No.: 09/273,979

(22) Filed: Mar. 22, 1999

(30) Foreign Application Priority Data

Mar. 25, 1998 (CH) .................................................. 0708/98

(51) Int. Cl.⁷ ..................... C07C 233/05; C07C 231/04
(52) U.S. Cl. ........................................ 564/200; 564/199
(58) Field of Search ................................. 564/200, 199

(56) References Cited

U.S. PATENT DOCUMENTS 2,714,117 A * 7/1955 Lacey et al. ................ 564/200
3,304,328 A * 2/1967 Pelley ........................ 564/200
5,523,486 A * 6/1996 Mack et al. ................. 564/200

FOREIGN PATENT DOCUMENTS

DE  2519036   11/1976
EP  0648738   4/1995

OTHER PUBLICATIONS

*Ullmann's Encyclopedia of Industrial Chemistry*, 5th Edition, vol. 15, p. 71.

* cited by examiner

*Primary Examiner*—Shailendra Kumar
(74) *Attorney, Agent, or Firm*—Fisher, Christen & Sabol

(57) ABSTRACT

Novel acetoacetarylamides in the form of a solidified melt which are in a form which can be used in industry and is easy to handle and which has a water content of from 3 to 15 percent by weight. These novel acetoacetarylamides have been used for the preparation of colored pigments or agrochemical active ingredients.

20 Claims, No Drawings

ACETOACETARYLAMIDES

BACKGROUND OF THE INVENTION

1. Field of the Invention

The invention relates to a novel process for the preparation of acetoacetarylamides of the general formula:

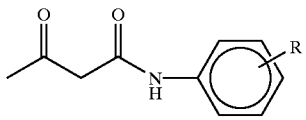

in which R is one or more substituents from the series alkyl, alkoxy or hydrogen.

Acetoacetarylamides are important starting materials for the preparation of colored pigments, but are also used for the preparation of agrochemical active ingredients (*Ulmann's Encyclopedia of Industrial Chemistry*, 5th Edition, vol. 15, p. 71).

2. Background Art

The preparation of acetoacetarylamides has been known for some time and is based on the reaction of diketene with corresponding aromatic amines in a variety of organic and aqueous solvents and solvent mixtures (*Ullmann's Encyclopedia of Industrial Chemistry*, 5th Edition, vol. 15, p. 71).

The process is usually carried out batchwise in water or aqueous solutions.

Accordingly, German Published Patent Application No. 2,519,036 discloses the preparation of various acetoacetarylamides by simultaneous metered addition of diketene and corresponding aromatic amine in the presence of water or aqueous solutions. The resulting acetoacetarylamide is cooled in the reaction mixture and left to crystallize out. Centrifugation and drying give the acetoacetarylamides in good yield and high purity.

Furthermore, European Published Patent Application No. 0648738 discloses a continuous process for the preparation of acetoacetarylamides. This involves continuously reacting diketene with the aromatic amine in a water/alcohol mixture with the reaction mixture having as long a residence time as possible in the reactor. The resulting acetoacetarylamide is isolated by crystallization of the product stream discharged from the reactor. The acetoacetarylamide prepared by the classic process satisfies all requirements in terms of quality and purity. It has, however, been found that for further processing, e.g., for pigment preparation, which usually involves the dissolution of the acetoacetarylides in aqueous alkalis, the finely crystalline powder form is more of a disadvantage. Thus, in addition to the undesired formation of dust, the slow dissolution rate in aqueous alkalis is somewhat unsatisfactory.

BROAD DESCRIPTION OF THE INVENTION

An object of the invention is to prepare acetoacetarylamides in a form which does not have the above-mentioned disadvantages. Moreover, an object of the invention is to provide an economic process which permits acetoacetarylamide preparation at a relatively low cost. The objects of the invention are achieved by the process of the invention and by the acetoacetarylamides in the form and with the properties according to the invention.

The acetoacetarylamides are defined by the general formula:

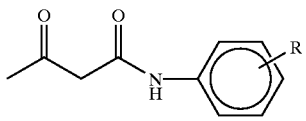

in which R is hydrogen or one or more substituents from the series alkyl, alkoxy or halogen, are a solidified melt in a form which can be used in industry and is easy to handle, and have a water content between 3 and 15 percent by weight.

An alkyl group is expediently taken to mean a $C_{1-4}$-alkyl group, namely, methyl, ethyl, n-propyl, isopropyl, n-butyl, isobutyl or t-butyl. A preferred alkyl is methyl. The alkoxy group has meanings corresponding to the alkyl group. Here too, preference is given to methoxy. Halogen represents fluorine, chlorine, bromine or iodine, preferably chlorine. R is particularly preferably an arylamide radical of aniline, o-anisidine, o-toluidine, m-xylidine, o-chloroaniline, 2,4-dimethoxyaniline, 4-isopropylaniline, 4-ethoxyaniline, 2,5-dimethoxyaniline or 4-chloro-2,5-dimethoxyaniline.

The term "form which can be used in industry and is easy to handle" includes those application forms which can be obtained from a solidified melt using methods customary in the expert field. Nonexhausted examples include: pastilles, flakes, tablets or prills. The dimension and size of such application forms is dependent on such pastilling, flaking, tabletting or prilling processes and can vary within a wide range. The novel acetoacetarylides also have improved flowability compared with an acetoacetarylide according to the prior art.

The bulk density of the novel acetoacetarylides is expediently in the range from 0.3 to 0.8 kg/l, preferably in the range from 0.5 to 0.7 kg/l.

The specified term "water content" can also mean a content of any mixture of water with an additional solubility promoter, which can originate from the reaction, such as, aliphatic carboxylic acids such as acetic acid, ketones such as acetone or ethyl methyl ketone, $C_1$–$C_4$-alcohols or glycols such as ethylene glycol.

The novel acetoacetarylides have a reduced characteristic melting point compared with the dried product.

The novel acetoacetarylamides dissolve in a 0.5 N sodium hydroxide solution at 20° C. in from approximately half to one third of the time required by a dried acetoacetarylide prepared according to the prior art.

Preferred acetoacetarylides with their characteristic properties are:

(a) acetoacetanilide, water content expediently from 5 to 15 percent by weight, preferably from 9 to 11 percent by weight; melting point expediently from 50° to 70° C., preferably from 57° to 62° C.; solubility in 500 ml of 0.5 N NaOH, 60 g pastilles having a diameter of 0.6 cm in from 10 to 20 minutes.

(b) o-Acetoacetanisidide, water content expediently from 3 to 12 percent by weight, preferably from 6 to 9 percent by weight; melting point expediently from 60° to 80° C., preferably from 72° to 75° C.; solubility in 500 ml of 0.5 N of NaOH, 60 g pastilles having a diameter of 0.6 cm in from 10 to 20 minutes.

(c) o-Acetoacetotoluidide, water content expediently from 5 to 15 percent by weight, preferably from 8 to 12 percent by weight; melting point expediently from 80° to 100° C., preferably from 82° to 94° C.; solubility in 700 ml of 0.5 N NaOH, 60 g pastilles having a diameter of 0.6 cm in from 10 to 20 minutes.

(d) m-Acetoacetoxylidide, water content expediently from 3 to 12 percent by weight, preferably from 4 to 8 percent by weight; melting point expediently from 65° to 85° C., preferably from 68° to 73° C.; solubility in 700 ml of 0.5 N NaOH, 60 g pastilles having a diameter of 0.6 cm in from 10 to 20 minutes.

(e) o-Acetoacetochloroanilide, water content expediently from 3 to 12 percent by weight, preferably from 5 to 8 percent by weight; melting point expediently from 75° to 95° C., preferably from 89° to 93° C.; solubility in 500 ml of 0.5 N NaOH, 60 g pastilles having a diameter of 0.6 cm in from 10 to 20 minutes.

The preparation of the novel acetoacetarylides initially takes place in a known manner by the reaction of diketene with the corresponding aromatic amine in the presence of water or aqueous solutions or water with a suitable solubility promoter, such as acetic acid. According to the present invention, the reaction is carried out such that the resulting acetoacetarylide is produced as a melt, the melt is removed from the reaction medium after the reaction is complete at the reaction temperature, and, after cooling, is converted into the form which can be used in industry and is easy to handle.

The preparation can either be carried out batchwise, for example, in a classic stirred apparatus, or continuously, for example, in a tubular reactor. The reaction is preferably carried out continuously in a tubular reactor.

It is particularly preferable to meter diketene and the corresponding aromatic aniline into a tubular reactor simultaneously to recirculated mother liquor such that the reaction temperature is maintained at from 50° to 100° C. The mother liquor expediently comprises at least 80 percent by weight of water, and is preferably exclusively water. After the reaction, in accordance with the preferred process at from 50° to 100° C., the aqueous mother liquor is removed and returned to the tubular reactor. The acetoacetarylide melt, which has a temperature of from 50° to 100° C., is then solidified by cooling and converted into the form which can be used in industry and is easy to handle. This can be carried out using, for example, drum coolers customary in the expert field, which are provided with a flaking device, with belt coolers, which are provided with a flaking device, or belt pastilling machines.

DETAILED DESCRIPTION OF THE INVENTION

EXAMPLE 1

Preparation of Acetoacetanilide (Comparative Example in Accordance with German Published Patent Application No. 2,519,036)

Water was introduced into a 1.5 l bench stirrer and adjusted to a temperature of 20° C. The stirrer was then rendered inert using nitrogen. Using two pumps, 133 g of aniline and 124 g of diketene were metered in over the course of 10 minutes. The addition of aniline was delayed by about 30 sec. At the end of the metered addition, the reaction temperature increased to 65° to 70° C. The mixture was then allowed to react for a further 30 minutes, and the reaction temperature dropped to 60° C. Vacuum cooling (450 to 120 mbar) was used to cool the mixture to 40° C., and the liquid acetoacetanilide began to crystallize, as a result of which the temperature immediately rose to about 58° C. The mixture was then cooled to 15° C. At 15° C., the solid product was centrifuged off, washed with 50 ml of water and dried at 50° C. under reduced pressure for 12 h. This method gave acetoacetanilide having a content of >99.5 percent (with a residual moisture content of <0.1 percent). The yield in terms of aniline was 97.1 percent, and in terms of diketene was 92.0 percent. A crystalline product having an average particle size of 450 to 500 μm was obtained. 50 g of the resulting acetoacetanilide (dry, 99.5 percent, water content <0.1 percent) dissolved completely at 20° C. in 500 ml of a 0.5 M aqueous sodium hydroxide solution in 25 minutes.

EXAMPLE 2

Preparation of the Solidified Melt of Acetoacetanilide (tubular reactor)

In a tubular reactor (length 80 cm, diameter 10 cm), 1300 ml of water was circulated at 62° C., and 0.200 g/s of aniline and 0.190 g/s of diketene (5 percent by weight excess) were metered in simultaneously. After the reaction mixture had passed through the tubular reactor, it was left in a separating vessel thermostatted at 62° C. The melt was then separated off from the aqueous phase. The aqueous phase was returned to the tubular reactor using a pump at a recirculation rate of 2250 ml/min. The melt which was separated off was immediately solidified and further processed according to Examples 4 to 6. This gave a melt having a water content of 11 percent by weight and a melting point of 62° C. Grinding the solidified melt and drying under reduced pressure for 12 h at 50° C. led to a crystalline acetoacetanilide having a content of <99.5 percent by weight (with a residual moisture content of <0.1 percent). The yield in terms of aniline was 99.1 percent, and in terms of diketene between 94.0 and 98.7 percent, depending on the diketene excess.

EXAMPLE 3

Preparation of the Solidified Melt of Acetoacetanilide (bench stirrer)

Water was introduced into a 1.5 l bench stirrer and adjusted to a temperature of 20° C. The stirrer was then rendered inert using nitrogen. Using two pumps, 133 g of aniline and 124 g of diketene were metered in over the course of 10 minutes. The addition of aniline was delayed by about 30 sec. At the end of the metered addition the reaction temperature increased to 65° to 70° C. The mixture was then allowed to react for a further 30 minutes, and the reaction temperature dropped to 60° C. The melt was run off and cooled thoroughly. This gave a melt having a water content of 10 percent by weight and a melting point of 61.5° C. Grinding the solidified melt and drying under reduced pressure for 12 h at 50° C. led to a crystalline acetoacetanilide having a content of >99.5 percent by weight (with a residual moisture content of <0.1 percent). The yield in terms of aniline was 80.5 percent, and in terms of diketene was 76 percent.

EXAMPLE 4

Flaking the Solidified Melt of Acetoacetanilide Using a Drum Cooler

The melt prepared according to Example 3 was continually dropped, at a temperature of 60° C., onto a rotating metal roller which was cooled to 0° C. using an external cooling circuit and had a smooth surface, a diameter of 30 cm and a rotation speed of 10 rpm, as a result of which it immediately solidified and, after a cooling stretch of 30 cm, was chipped off the roller using a knife. This gave white flakes having an average thickness of 0.08 mm and an average diameter of from 0.5 mm to 500 mm. 55.6 g of the resulting acetoacetanilide (moist, content of acetoacetanilide 89.5 percent, water content 10 percent) dissolved completely at 20° C. in 500 ml of a 0.5 M aqueous sodium hydroxide solution in about 15 minutes.

EXAMPLE 5

Flaking the Solidified Melt of Acetoacetanilide Using a Belt Cooler

The melt prepared according to Example 3 was continually dropped, at a temperature of 60° C., onto a rotating metal belt, which was cooled to 0° C. using an external cooling circuit and had a smooth surface, a width of 30 cm and a rotation speed of 10 m/min., as a result of which it immediately solidified and, after a cooling stretch of 4 m, was chipped off the belt cooler using a knife. This gave white flakes having an average thickness of 0.08 cm and an average diameter of from 0.5 mm to 500 mm. 55.6 g of the resulting acetoacetanilide (moist, content of acetoacetanilide 89.5 percent, water content 10 percent) dissolved completely at 20° C. in 500 ml of a 0.5 M aqueous sodium hydroxide solution in about 17 minutes.

EXAMPLE 6

Pastilling the Solidified Melt of Acetoacetanilide Using a Belt Pastilling Machine The melt prepared according to Example 3 was continually dropped, at a temperature of 60° C., using a device suitable for the preparation of pastilles, onto a rotating metal belt, which was cooled to 0° C. by means of an external cooling circuit and had a smooth surface, a width of 30 cm and a rotation speed of 10 m/min, as a result of which it immediately solidified and, after a cooling stretch of 4 m, was removed from the belt. This gave white pastilles having an average thickness of 0.05 cm and an average diameter of 0.6 cm. 55.6 g of the resulting acetoacetanilide (moist, content of acetoacetanilide 89.5 percent, water content 10 percent) dissolved completely at 20° C. in 500 ml of a 0.5 M aqueous sodium hydroxide solution in about 17 minutes.

EXAMPLE 7

Preparation of the Solidified Melt of o-acetoacetanisidide

Following the procedure as in Example 2, the corresponding reaction of diketene and o-anisidine gave a melt having a water content of 7 percent by weight and a melting point of 74° C., which was processed to give pastilles according to Example 6. 60 g of the resulting o-acetoacetanisidide (moist, o-acetoacetaniside content 91.8 percent, water content 8 percent) dissolved at 20° C. in 500 ml of a 0.5 M aqueous sodium hydroxide solution in about 20 minutes.

EXAMPLE 8

Preparation of the Solidified Melt of o-acetoacetotoluidide

Following the procedure as in Example 2, the corresponding reaction of diketene and o-totoluidine gave a melt having a water content of 10 percent by weight and a melting point of 85° C., which was processed to give pastilles according to Example 6. 60 g of the resulting o-acetoacetotoluidide (moist, o-acetoacetotoluidide content 89.6 percent, water content 10 percent) dissolved at 20° C. in 700 ml of a 0.5 M aqueous sodium hydroxide solution in about 19 minutes.

EXAMPLE 9

Preparation of the Solidified Melt of m-acetoacetoxylidide

As in Example 2, the corresponding reaction of diketenes and m-xylidine gave a melt having a water content of 7 percent by weight and a melting point of 74° C., which was processed to give pastilles according to Example 6. 60 g of the resulting m-acetoacetoxylidide (moist, m-acetoacetoxylidide content 92.5 percent, water content 7 percent) dissolved at 20° C. in 700 ml of a 0.5 M aqueous sodium hydroxide solution in about 18 minutes.

EXAMPLE 10

Preparation of the Solidified Melt of o-Acetoacetochloroanilide

As in Example 2, the corresponding reaction of diketene and o-chloroaniline gave a melt having a water content of 7 percent by weight and a melting point of 90° C., which was processed to give pastilles according to EXAMPLE 6. 60 g of the resulting o-acetoacetochloroanilide (moist, o-acetoacetochloroanilide content 92.7 percent, water content 7 percent) dissolved at 20° C. in 500 ml of a 0.5 M aqueous sodium hydroxide solution in about 18 minutes.

What is claimed is:

1. An acetoacetarylamide defined by the formula:

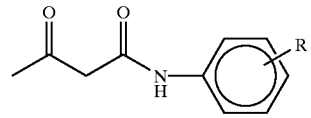

in which R is hydrogen or at least one substituent from the series alkyl, alkoxy or halogen, as a solidified melt in a form which can be used in industry and is easy to handle, which has a water content between 3 and 15 percent by weight.

2. An acetoacetarylide according to claim 1 in the form of flakes, pills, pastilles or tablets.

3. An acetoacetarylide according to claim 2 having a bulk density between 0.3 kg/l and 0.8 kg/l.

4. Acetoacetanilide as the acetoacetarylide according to claim 3 having a water content of from 5 to 15 percent by weight and a melting point of from 50° to 70° C.

5. o-Acetoacetanisidide as the acetoacetarylide according to claim 3 having a water content of from 3 to 12 percent by weight and a melting point of from 50° to 80° C.

6. o-Acetoacetotoluidide as the acetoacetarylide according to claim 3 having a water content of from 5 to 15 percent by weight and a melting point of from 80° to 100° C.

7. m-Acetoacetoxylidide as the acetoacetarylide according to claim 3 having a water content of from 3 to 12 percent by weight and a melting point of from 65° to 85° C.

8. o-Acetoacetochloroanilide as the acetoacetarylide according to claim 3 having a water content of from 3 to 12 percent by weight and a melting point of from 75° to 95° C.

9. Acetoacetanilide as the acetoacetarylide according to claim 1 having a water content of from 5 to 15 percent by weight and a melting point of from 50° to 70° C.

10. o-Acetoacetanisidide as the acetoacetarylide according to claim 1 having a water content of from 3 to 12 percent by weight and a melting point of from 50° to 80° C.

11. o-Acetoacetotoluidide as the acetoacetarylide according to claim 1 having a water content of from 5 to 15 percent by weight and a melting point of from 80° to 100° C.

12. m-Acetoacetoxylidide as the acetoacetarylide according to claim 1 having a water content of from 3 to 12 percent by weight and a melting point of from 65° to 85° C.

13. o-Acetoacetochloroanilide as the acetoacetarylide according to claim 1 having a water content of from 3 to 12 percent by weight and a melting point of from 75° to 95° C.

14. An acetoacetarylide according to claim 1, which has been obtained by reaction of diketene with a corresponding aromatic amine in the presence of water or aqueous solution, the reaction being carried out such that the resulting acetoacetarylide is produced as a melt, the melt is removed from the reaction medium at reaction temperature when the reaction is complete, and, after cooling, is converted into the form which can be used in industry and is easy to handle.

15. An acetoacetarylide according to claim 14, which has been obtained by reaction of diketene and the corresponding aromatic amine in the presence of an aqueous mother liquor, at least 80 percent by weight of which is water, the diketene and the aromatic amine being metered into a tubular reactor simultaneously to recirculated mother liquor such that the reaction temperature is maintained at from 50° to 100° C., the mother liquor is separated off after the reaction at the given temperature of from 50° to 100° C. and returned to the tubular reactor, and the resulting acetoacetarylide melt, which has a temperature of from 50° to 100° C., is cooled and converted into the form which can be used in industry and is easy to handle.

16. A process for the preparation of an acetoacetarylide according to claim 1, reaction of diketene with corresponding aromatic amine in the presence of water or aqueous solution, characterized in that the reaction is carried out such that the resulting acetoacetarylide is produced as a melt, the melt is removed from the reaction medium after the reaction is complete at the reaction temperature, and after cooling, is converted into the form which can be used in industry and is easy to handle.

17. An acetoacetarylide according to claim 2, which has been obtained by reaction of diketene with a corresponding aromatic amine in the presence of water or aqueous solution, the reaction being carried out such that the resulting acetoacetarylide is produced as a melt, the melt is removed from the reaction medium at the reaction temperature when the reaction is complete, and after cooling, is converted into the form which can be used in industry and is easy to handle.

18. An acetoacetarylide according to claim 17, which has been obtained by reaction of diketene and the corresponding aromatic amine in the presence of an aqueous mother liquor, at least 80 percent by weight of which is water, the diketene and the aromatic amine being metered into a tubular reactor simultaneously to recirculated mother liquor such that the reaction temperature is maintained at from 50° to 100° C., the mother liquor is separated off after the reaction at the given temperature of from 50° to 100° C. and returned to the tubular reactor, and the resulting acetoacetarylide melt, which has a temperature of from 50° to 100° C., is cooled and converted into the form which can be used in industry and is easy to handle.

19. A process for the preparation of an acetoacetarylide according to claim 2, by reaction of diketene with corresponding aromatic amine in the presence of water or aqueous solution, characterized in that the reaction is carried out such that the resulting acetoacetarylide is produced as a melt, the melt is removed from the reaction medium after the reaction is complete at the reaction temperature, and after cooling, is converted into the form which can be used in industry and is easy to handle.

20. A process for the preparation of an acetoacetarylide by the reaction of diketene and corresponding aromatic amine in the presence of an aqueous mother liquor, at least 80 percent by weight of which is water, characterized in that the diketene and the aromatic amine are metered into a tubular reactor simultaneously to recirculated mother liquor such that the reaction temperature is maintained at from 50° to 100° C., the mother liquor is separated off after the reaction at the given temperature of from 50° to 100° C. and returned to the tubular reactor, and the resulting acetoacetanilide melt, which has a temperature of from 50° to 100° C., is cooled and converted into the form which can be used in industry and is easy to handle.

* * * * *